US00PP18654P2

(12) United States Plant Patent
Payne

(10) Patent No.: US PP18,654 P2
(45) Date of Patent: Mar. 25, 2008

(54) ***HELIANTHUS* PLANT NAMED 'SLG DS 05'**

(50) Latin Name: *Helianthus debilis*
Varietal Denomination: SLG DS 05

(76) Inventor: Christopher Payne, 175 S. Orchard St., Ormond Beach, FL (US) 32174

( * ) Notice: Subject to any disclaimer, the term of this patent is extended or adjusted under 35 U.S.C. 154(b) by 0 days.

(21) Appl. No.: 11/478,052

(22) Filed: Jun. 29, 2006

(51) Int. Cl.
*A01H 5/00* (2006.01)

(52) U.S. Cl. ..... Plt./263

(58) Field of Classification Search ..... Plt./263
See application file for complete search history.

(56) References Cited

PUBLICATIONS

University of Florida, Cooperative Extension Service; Fact Sheet FPS–245; '*Helianthus debilis*' Oct. 1999. (3 pages total).*

* cited by examiner

*Primary Examiner*—Kent Bell
*Assistant Examiner*—S. B. McCormick-Ewoldt

(57) ABSTRACT

A new and distinct *Helianthus* plant cultivar is disclosed, characterized by a compact growth habit, bright yellow ray florets, a dark, purple-brown center and a short node length.

1 Drawing Sheet

Latin name of the genus and species: *Helianthus debilis*.
Variety denomination: 'SLG DS 05'.

BACKGROUND OF THE INVENTION

The new cultivar 'SLG DS 05' was discovered as a naturally occurring whole plant mutation within a population of unnamed *Helianthus* plants. The new cultivar was discovered in 2001 in Ormond Beach, Fla.

Asexual reproduction of the new cultivar 'SLG DS 05' by vegetative terminal tip cuttings was performed in Ormond Beach, Fla. and Oxnard, Calif., and has shown that the unique features of this new cultivar are stable and reproduced true to type on successive generations.

SUMMARY OF THE INVENTION

The cultivar 'SLG DS 05' has not been observed under all possible environmental conditions. The phenotype may vary somewhat with variations in environment such as temperature, daylength, and light intensity, without, however, any variance in genotype.

The following traits have been repeatedly observed and are determined to be the unique characteristics of 'SLG DS 05'. These characteristics in combination distinguish 'SLG DS 05' as a new and distinct *Helianthus* cultivar:

1. A compact habit;
2. Bright yellow ray florets;
3. A dark, purple-brown center and;
4. A short node length.

Plants of the new cultivar 'SLG DS 05' are similar to plants of the parent variety, *Helianthus debilis* in most horticultural characteristics, however plants of the new cultivar 'SLG DS 05' have much shorter nodes than the wild varieties and a more compact habit.

In comparison to *Helianthus debilis* 'Orion' (not patented), the new cultivar 'SLG DS 05' has much shorter nodes and a more compact growth habit.

BRIEF DESCRIPTION OF THE PHOTOGRAPH

The accompanying photograph illustrates in full color a typical plant of 'SLG DS 05' grown in a 2 gallon container. One cutting was used in the pot, planted mid May and grown in a greenhouse. The colors are as nearly true as is reasonably possible in a color representation of this type.

DETAILED BOTANICAL DESCRIPTION

In the following description, color references are made to The Royal Horticultural Society Colour Chart except where general terms of ordinary dictionary significance are used. The following observations and measurements describe 'SLG DS 05' plants grown in Oxnard, Ventura County, Calif., during the months of May through October. The growing temperature ranged from 12° C. to 15° C. at night to 12° C. to 20° C. during the day. Measurements and numerical values represent averages of typical flowering types.

Botanically classification: *Helianthus debilis* cultivar 'SLG DS 05.'
Commercial classification: Beach sunflower.

PROPAGATION

Time to rooting: 14 to 20 days at approximately 24° C.
Root description: Fine, fibrous.

PLANT

Growth habit: Spreading herbaceous perennial.
Height: Approximately 30 cm.
Plant spread: Approximately 80 cm.
Growth rate: Fast.
Branching characteristics: Free Branching.
Lateral branch habit: Ungulate.
Length of lateral branches: Approximately 35 cm.
Diameter of lateral branches: Approximately 5 mm.
Texture of lateral branches: Lightly pubescent.
Number of leaves per lateral branch: Approximately 23.
Age of plant described: Approximately 146 days.

FOLIAGE

Leaf:
*Arrangement.*—Alternate.
*Average length.*—Approximately 4.4 cm.
*Average width.*—Approximately 2.9 cm.
*Shape of blade.*—Ovate.
*Apex.*—Acute.
*Base.*—Cordate.
*Attachment.*—Stalked.
*Margin.*—Dentate.
*Texture of top surface.*—Lightly pubescent.
*Texture of bottom surface.*—Roughly pubescent.
*Leaf internode length.*—Approximately 3 cm.
*Color.*—Young foliage upper side: Near Green 137C. Young foliage under side: Near Green 137C. Mature foliage upper side: Near Green 137A. Mature foliage under side: Near Green 137D.
*Venation.*—Type: Palmately net. Venation color upper side: Near Green 139D. Venation color under side: Near Green 139D.

Petiole:
*Average length.*—Approximately 3 cm.
*Color.*—Near Green 139D.
*Diameter.*—Approximately 0.01 cm.

BLOOM

Inflorescence:
*Flowering habit.*—Flowering continuous sporadically throughout the year with more flowers with temperature above 25° C.
*Inflorescence form.*—Daisy.
*Natural flowering season.*—Early spring to fall.
*Number of inflorescences per lateral branch.*—Approximately 1.
*Inflorescence diameter.*—Approximately 5.8 cm.
*Inflorescence depth.*—Approximately 2 cm.
*Longevity of a single inflorescence.*—Approximately 10 to 20 days.
*Persistence.*—Persistent.

Ray florets:
*Appearance.*—Matte.
*Texture.*—Smooth.
*Average number of ray florets per inflorescence.*—13.
*Shape.*—Oblanceolate.
*Aspect.*—Flat.
*Margin.*—Entire.
*Apex.*—Acute.
*Length.*—Approximately 2.4 cm.
*Width.*—Approximately 1 cm.
*Color.*—Upper surface at first opening: Near Yellow 2A. Upper surface at maturity: Near Yellow 14A. Upper surface at fading: Near Yellow 14A. Under surface at first opening: Near Yellow 2A. Under surface at maturity: Near Yellow 9A. Under surface at fading: Near Yellow 13A.

Disc florets:
*Appearance.*—Matte.
*Texture.*—Smooth.
*Average number of florets per disc.*—Approximately 80.
*Shape.*—Cylindric with globular base.
*Apex.*—Obtuse.
*Average length.*—Approximately 0.04 cm.
*Average width.*—Approximately 0.01 cm.
*Color.*—At first opening: Near Greyed-Purple 187A. At maturity: Near Greyed-Purple 187A. At fading: Near Greyed-Purple 187A.

Peduncle:
*Length.*—At terminal end (shortest): Approximately 12 cm. At lateral end (longest): Approximately 15 cm.
*Angle to stem.*—Acute.
*Strength.*—Moderate.
*Color.*—Near Greyed-Orange 177A.
*Habit.*—Upright ungulating.
*Diameter.*—Approximately 0.01 cm.
*Surface texture.*—Lightly pubescent.

Inflorescence bud:
*Length.*—Approximately 1.5 cm.
*Diameter.*—Approximately 1 cm.
*Form.*—Globular with prominent phyllaries larger than bud.
*Color.*—Near Yellow-Green 144A.

Involucral bracts (phyllaries):
*Appearance.*—Matte.
*Texture.*—Lightly pubescent.
*Number.*—Approximately 23.
*Shape.*—Lanceolate.
*Margin.*—Entire.
*Apex.*—Narrowly acuminate.
*Length.*—Approximately 0.08 cm.
*Width.*—Approximately 0.02 cm.
*Color.*—Upper side: Near Green 137B. Under side: Near Green 137D.

Fragrance: None detected.

REPRODUCTIVE ORGANS

Ray florets:
*Number of pistils per floret.*—1.
*Stigma shape.*—2 branched.
*Stigma color.*—Near Yellow 14A.
*Style color.*—Near Yellow-Green 154C.
*Style length.*—Approximately 0.03 cm.
*Stamens.*—Absent.

Disc florets:
*Number of pistils per floret.*—1.
*Stigma shape.*—Linear.
*Stigma color.*—Near Greyed-Purple 187A.
*Style length.*—Approximately 0.03.
*Style color.*—Near Yellow 13C.
*Number of stamens per floret.*—Approximately 5 fused.
*Anther shape.*—Tubular.
*Anther color.*—Near Greyed-Purple 187A.
*Pollen color.*—Near Yellow 13B.

OTHER CHARACTERISTICS

Disease resistance: Neither resistance nor susceptibility to diseases or pests has been observed in this variety.

Drought tolerance/cold tolerance: Flowering plants are hardy to low temperatures about −2° C. Non-flowering plants are hardy in the approximate range of 3° C. to −6° C., depending upon duration of cold and amount of moisture in the soil. With adequate water plants are hardy to a high temperature of 45° C. The drought tolerance is high and cold tolerance for the roots is to 10° F.

Fruit/seed production: Commercially, this plant is not used or observed in a stage where seeds would be produced. Therefore, seed production has not been observed.

What is claimed is:

1. A new and distinct cultivar of *Helianthus* plant named 'SLG DS 05' as herein illustrated and described.

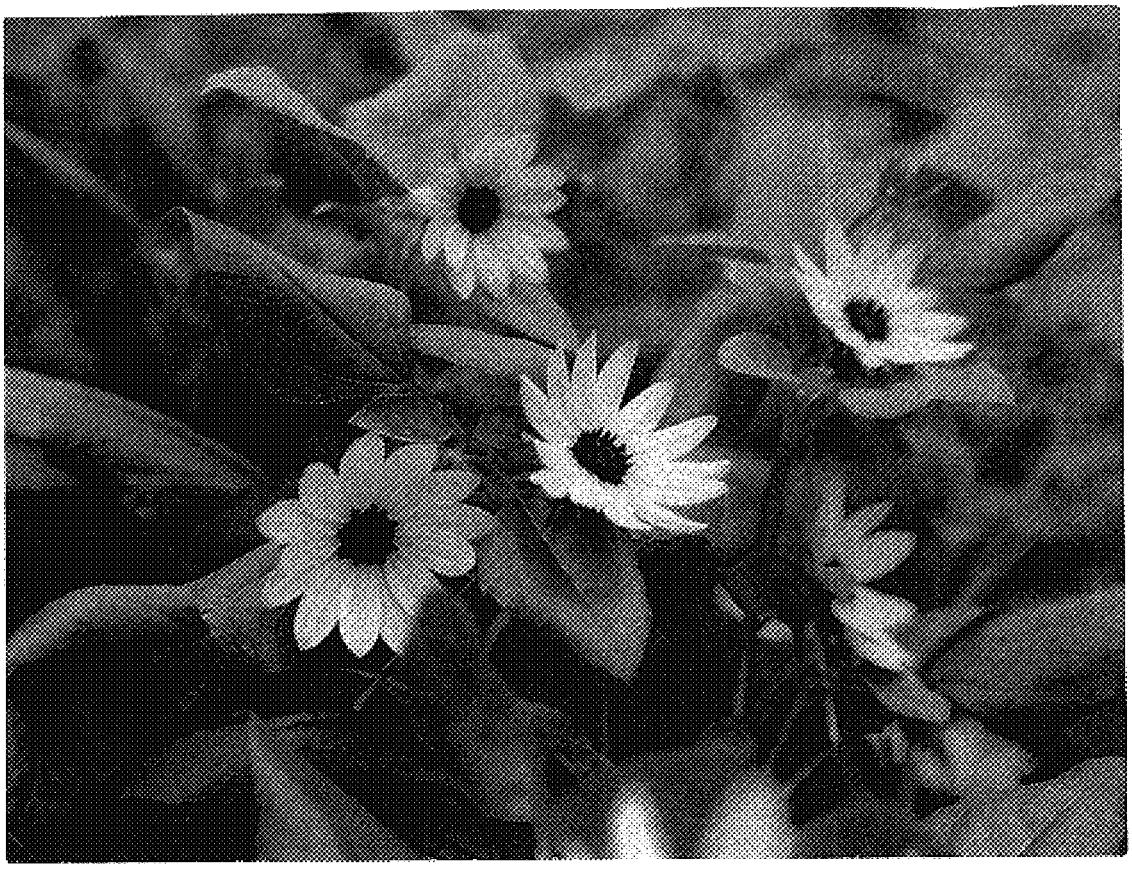

* * * * *